US011957686B2

(12) United States Patent
Tabuteau

(10) Patent No.: US 11,957,686 B2
(45) Date of Patent: Apr. 16, 2024

(54) COMPOSITIONS FOR DELIVERY OF REBOXETINE

(71) Applicant: AXSOME THERAPEUTICS, INC., New York, NY (US)

(72) Inventor: Herriot Tabuteau, New York, NY (US)

(73) Assignee: Axsome Therapeutics, Inc., New York, NY (US)

( * ) Notice: Subject to any disclaimer, the term of this patent is extended or adjusted under 35 U.S.C. 154(b) by 0 days.

(21) Appl. No.: 17/848,685

(22) Filed: Jun. 24, 2022

(65) Prior Publication Data
US 2022/0313699 A1 Oct. 6, 2022

Related U.S. Application Data

(63) Continuation of application No. 17/064,016, filed on Oct. 6, 2020, now abandoned, which is a continuation-in-part of application No. PCT/US2019/037500, filed on Jun. 17, 2019.

(60) Provisional application No. 62/837,002, filed on Apr. 22, 2019, provisional application No. 62/688,333, filed on Jun. 21, 2018, provisional application No. 62/686,075, filed on Jun. 17, 2018.

(51) Int. Cl.
*A61K 9/20* (2006.01)
*A61K 9/24* (2006.01)
*A61K 9/28* (2006.01)
*A61K 31/5375* (2006.01)

(52) U.S. Cl.
CPC ........ *A61K 31/5375* (2013.01); *A61K 9/2013* (2013.01); *A61K 9/2027* (2013.01); *A61K 9/2054* (2013.01); *A61K 9/209* (2013.01); *A61K 9/282* (2013.01); *A61K 9/2846* (2013.01); *A61K 9/2866* (2013.01)

(58) Field of Classification Search
CPC ........ A61K 9/20; A61K 9/2004; A61K 9/205; A61K 9/2054; A61K 9/2081; A61K 9/2086; A61K 9/209
See application file for complete search history.

(56) References Cited

U.S. PATENT DOCUMENTS

| | | | |
|---|---|---|---|
| 6,228,398 B1 | 5/2001 | Devane et al. | |
| 6,395,788 B1 | 5/2002 | Inglehart | |
| 6,441,038 B1 | 8/2002 | Loder et al. | |
| 6,465,458 B1 | 10/2002 | Wong et al. | |
| 6,485,746 B1 | 11/2002 | Campbell et al. | |
| 6,610,690 B2 | 8/2003 | Wong et al. | |
| 6,622,036 B1 | 9/2003 | Suffin | |
| 6,632,451 B2 | 10/2003 | Penhasi et al. | |
| 6,642,235 B2 | 11/2003 | Wong et al. | |
| 6,703,389 B2 | 3/2004 | Wong et al. | |
| 6,987,107 B2 | 1/2006 | Wong et al. | |
| 7,241,762 B2 | 7/2007 | Wong et al. | |
| 7,276,503 B2 | 10/2007 | Wong et al. | |
| 7,317,011 B2 | 1/2008 | Wong et al. | |
| 7,338,953 B2 | 3/2008 | Wong et al. | |
| 7,723,334 B2 | 5/2010 | Wong et al. | |
| 8,512,751 B2* | 8/2013 | Rariy | A61P 25/00 424/488 |
| 8,562,951 B2 | 10/2013 | Suffin et al. | |
| 9,034,874 B2 | 5/2015 | Auberson et al. | |
| 9,211,293 B2 | 12/2015 | Deaver et al. | |
| 9,216,182 B2 | 12/2015 | Wang et al. | |
| 9,359,290 B2 | 6/2016 | Khayrallah et al. | |
| 9,624,192 B2 | 4/2017 | Auberson et al. | |
| 9,750,734 B2 | 9/2017 | Mouthon et al. | |
| 9,763,884 B2 | 9/2017 | Bloemers et al. | |
| 11,020,402 B2 | 6/2021 | Tabuteau | |
| 11,135,226 B2 | 10/2021 | Tabuteau | |
| 11,185,547 B2 | 11/2021 | Tabuteau | |
| 11,351,175 B2 | 6/2022 | Tabuteau | |
| 11,364,245 B2 | 6/2022 | Tabuteau | |
| 2003/0040464 A1 | 2/2003 | Wong et al. | |
| 2006/0039890 A1 | 2/2006 | Renshaw et al. | |
| 2008/0020039 A1 | 1/2008 | Parikh et al. | |
| 2008/0103145 A1 | 5/2008 | Wong et al. | |
| 2008/0261984 A1* | 10/2008 | Hughes | A61K 31/5375 514/239.2 |
| 2009/0023705 A1 | 1/2009 | Roberts et al. | |
| 2009/0275562 A1 | 11/2009 | Rao et al. | |
| 2011/0052648 A1 | 3/2011 | Avramoff et al. | |
| 2012/0035121 A1 | 2/2012 | Rudnic et al. | |

(Continued)

FOREIGN PATENT DOCUMENTS

| CL | 200001765 | 7/2001 |
|---|---|---|
| CL | 200802868 | 1/2009 |

(Continued)

OTHER PUBLICATIONS

Larrosa et al (Stimulant and Anticataplectic Effects of Reboxetine in Patients with Narcolepsy: A Pilot Study; Clinical Pharmacology; Sleep, vol. 24, No. 3, 2001) (Year: 2001).*

Larrosa, O. et al., Stimulant and Anticataplectic Effects of Reboxetine in Patients with Narcolepsy: A Pilot Study, Sleep, 24(3), 282-285, May 2001.

Summary of Product Characteristics, EDRONAX (reboxetine), last updated on UK electronic Medicines Compendium (eMC), Oct. 23, 2015.

Hajos, M. et al., The Selective Norepinephrine Reuptake Inhibitor Antidepressant Reboxetine: Pharmacological and Clinical Profile, CNS Drug Reviews, 10(1), 23-44, Mar. 2004.

(Continued)

*Primary Examiner* — Micah Paul Young
(74) *Attorney, Agent, or Firm* — Maschoff Brennan; Brent A. Johnson; David Old

(57) ABSTRACT

Described herein are methods for the administration of reboxetine, or a pharmaceutically acceptable salt thereof, to a human being in need thereof, resulting in a first maximum plasma concentration and a second maximum plasma concentration, wherein the two maxima are separated by a time period of about 2 hours to about 6 hours.

20 Claims, No Drawings

(56) References Cited

U.S. PATENT DOCUMENTS

| | | |
|---|---|---|
| 2013/0017262 A1 | 1/2013 | Mullen et al. |
| 2014/0275244 A1 | 9/2014 | Khayrallah et al. |
| 2016/0244426 A1 | 8/2016 | Auberson et al. |
| 2019/0381056 A1 | 12/2019 | Tabuteau |
| 2020/0147093 A1 | 5/2020 | Tabuteau |
| 2020/0147094 A1 | 5/2020 | Tabuteau |
| 2020/0147095 A1 | 5/2020 | Tabuteau |
| 2020/0147096 A1 | 5/2020 | Tabuteau |
| 2021/0015823 A1 | 1/2021 | Tabuteau |
| 2021/0100808 A1 | 4/2021 | Tabuteau |
| 2021/0100809 A1 | 4/2021 | Tabuteau |
| 2021/0169893 A1 | 6/2021 | Tabuteau |
| 2021/0252007 A1 | 8/2021 | Tabuteau |
| 2021/0369722 A1 | 12/2021 | Tabuteau |
| 2022/0249501 A1 | 8/2022 | Tabuteau |
| 2022/0280524 A1 | 9/2022 | Tabuteau |
| 2022/0362252 A1 | 11/2022 | Tabuteau |

FOREIGN PATENT DOCUMENTS

| | | |
|---|---|---|
| EP | 1632235 A2 | 3/2006 |
| EP | 1536791 B1 | 1/2010 |
| EP | 2514417 A2 | 10/2012 |
| WO | 1995028148 A1 | 10/1995 |
| WO | 0039072 A1 | 7/2000 |
| WO | 0101973 A2 | 1/2001 |
| WO | 2001001973 A2 | 1/2001 |
| WO | 0147503 A1 | 7/2001 |
| WO | 0162236 A2 | 8/2001 |
| WO | 2006069030 A1 | 6/2006 |
| WO | 2008137923 A2 | 11/2008 |
| WO | 2009049215 A1 | 4/2009 |
| WO | 2009062318 A1 | 5/2009 |
| WO | 2011107749 A2 | 9/2011 |
| WO | 2011107750 A2 | 9/2011 |
| WO | 2011107755 A2 | 9/2011 |
| WO | 2018200775 A1 | 11/2018 |
| WO | 2019245975 A1 | 12/2019 |
| WO | 2020081461 A1 | 4/2020 |

OTHER PUBLICATIONS

Schmidt, C. et al., The norepinephrine reuptake inhibitor reboxetine is more potent in treating murine narcoleptic episodes than the serotonin reuptake inhibitor escitalopram, Behavioural Brain Research, 308, 205-210, Jul. 2016.
Sepede, G. et al., Reboxetine in clinical practice: a review, Clin Ter., 163(4), e255-e262, Jul. 2012.
U.S. National Library of Medicine, ClinicalTrials.gov Identifier NCT03881852, Clinical Outcomes in Narcolepsy and Cataplexy: An Evaluation of Reboxetine Treatment (CONCERT), 2019; downloaded from: https://clinicaltrials.gov/ct2/show/NCT03881852 on Jul. 17, 2019.
Aloe, F. et al., Brazilian guidelines for the treatment of narcolepsy, Brazilian Journal of Psychiatry, 32(3), 305-314, Sep. 2010.
Doksat et al., A Case of Profound Weight Loss Secondary to use of Reboxetine, J Child Adolesc Behav 2014, 2:3, 2014.
Shands, Drugs & Therapy Bulletin, vol. 21, No. 10, 2007.
Preetha et al., Biphasic Drug Delivery in Controlled Release Formulations—A Review. IJ PT, 6(4), 3046-3060, Apr. 2015.
Reboxetine, Package Leaflet: Information for the User, 2017.
Sankar et al., What is a missed dose? Implications for construct validity and patient adherence, AIDS Care, 19(6), 775-780, Jul. 2007.
Tabuteau, International Search Report and Written Opinion, PCT/US 2019/056134, dated Jan. 30, 2020.
U.S. Appl. No. 16/740,329, filed Jan. 10, 2020 First Named Inventor: Herriot Tabuteau Assignee: Axsome Therapeutics, Inc.
U.S. Appl. No. 16/740,409, filed Jan. 11, 2020 First Named Inventor: Herriot Tabuteau Assignee: Axsome Therapeutics, Inc.
U.S. Appl. No. 16/740,410, filed Jan. 11, 2020 First Named Inventor: Herriot Tabuteau Assignee: Axsome Therapeutics, Inc.
U.S. Appl. No. 16/740,411, filed Jan. 11, 2020 First Named Inventor: Herriot Tabuteau Assignee: Axsome Therapeutics, Inc.
U.S. Appl. No. 17/116,874, filed Dec. 9, 2020 First Named Inventor: Herriot Tabuteau Assignee: Axsome Therapeutics, Inc.
U.S. Appl. No. 17/119,792, filed Dec. 11, 2020 First Named Inventor: Herriot Tabuteau Assignee: Axsome Therapeutics, Inc.
Daniels et al., Health-related quality of life in narcolepsy, J. Sleep Res., 10(1), 75-81, Mar. 2001.
Tabuteau, International Search Report and Written Opinion, PCT/US2019/037500, dated Oct. 31, 2019.
Tabuteau, International Preliminary Report on Patentability, PCT/US2019/037500, dated Dec. 30, 2020.
Sateia et al., International Classification of Sleep Disorders, Chest, 146(5), 1387-1394, Nov. 2014.
Kallweit et al., Patient-Reported Measures of Narcolepsy: The Need for Better Assessment, Journal of Clinical Sleep Medicine, 13(5), 737-744, 2017.
U.S. Appl. No. 16/514,948, filed Jul. 17, 2019 First Named Inventor: Herriot Tabuteau Assignee: Axsome Therapeutics, Inc.
U.S. Appl. No. 17/064,016, filed Oct. 6, 2020 First Named Inventor: Herriot Tabuteau Assignee: Axsome Therapeutics, Inc.
U.S. Appl. No. 17/177,554, filed Feb. 17, 2021 First Named Inventor: Herriot Tabuteau Assignee: Axsome Therapeutics, Inc.
Tabuteau, International Search Report and Written Opinion, PCT/US 2020/062560, dated Feb. 18, 2021.
Tabuteau, International Preliminary Report on Patentability, PCT/US 2019/056134, dated Apr. 29, 2021.
U.S. Appl. No. 17/245,644, filed Apr. 30, 2021 First Named Inventor: Herriot Tabuteau Assignee: Axsome Therapeutics, Inc.
Thorpy, Recently Approved and Upcoming Treatments for Narcolepsy, CNS Drugs, 34: 9-27, 2020.
Szabo et al. Neurobiological and Immunogenetic Aspects of Narcolepsy: Implications for Pharmacotherapy, Sleep Med Rev. 43: 23-36, Feb. 2019.
U.S. Appl. No. 17/398,368, filed Aug. 10, 2021 First Named Inventor: Herriot Tabuteau Assignee: Axsome Therapeutics, Inc.
Hublin et al., The Ullanlinna Narcolepsy Scale: validation of a measure of symptoms in the narcoleptic syndrome, Journal of Sleep Research, 3(1), 52-59, Mar. 1994.
Ullanlinna Narcolepsy Scale; the printable version accessed online at: healthysleep.med.harvard.edu/narcolepsy/diagnosing-narcolepsy/narcolepsy-self-evaluation, content last updated Feb. 2018.
European Extended Search Report and Written Opinion for related application 19874099.5, dated Nov. 26, 2021.
Garcia-Borreguero, D. et al., Effects of Reboxetine in Narcolepsy-Cataplexy: Preliminary findings on 14 patients, Sleep, vol. 24, No. Abstract Supplement, pp. A323-A324, Jun. 2001.
O'Gorman, C. et al., Scientific Rational and Clinical Development of AXS-12 for Narcolepsy, Sleep, vol. 42, No. Abstract Supplement, p. A24, Jan. 2019.
Szakacs, Z et al., Safety and efficacy of pitolisant on cataplexy in patients with narcolepsy: a randomised, double-blind, placebo-controlled trial, The Lancet Neurology, 16(3), 200-207, Mar. 2017.
Berro, L.F. et al., A journey through narcolepsy diagnosis: From ICSD 1 to ICSD 3, Sleep Science, 7(1), Mar. 2014.
Tabuteau, International Preliminary Report on Patentability, PCT/US2020/062560, dated Jun. 16, 2022.

* cited by examiner

COMPOSITIONS FOR DELIVERY OF REBOXETINE

CROSS REFERENCE TO RELATED APPLICATIONS

This application is a continuation of U.S. application Ser. No. 17/064,016, filed on Oct. 6, 2020; which is a continuation-in-part of International Pat. App. No. PCT/US2019/037500, filed Jun. 17, 2019; which claims the benefit to U.S. Provisional Pat. App. Nos. 62/686,075, filed Jun. 17, 2018; 62/688,333, filed Jun. 21, 2018; and 62/837,002, filed Apr. 22, 2019; all of which are incorporated by reference in their entirety.

FIELD

This disclosure relates to methods of administering or delivering reboxetine to human beings.

BACKGROUND

Reboxetine is a norepinephrine reuptake inhibitor that is marketed as an antidepressant, and sold in as an oral drug sold under the brand name Edronax®.

SUMMARY

This disclosure recognizes a need for dosage forms comprising reboxetine with different pharmacokinetic properties. The present disclosure also relates to the use of such dosage forms for the treatment of one or more conditions in a subject suitable for treatment by reboxetine or pharmaceutically acceptable salts thereof.

In human patients, reboxetine is rapidly absorbed, and peak levels are observed within about 2 hours of dosing. Due to its rapid absorption and metabolism, it is desirable to provide different formulations of reboxetine, or pharmaceutically acceptable salts of reboxetine, that may achieve multiple drug concentration maxima within a daily dosage regimen.

The present disclosure describes methods for providing reboxetine to the blood of a human being comprising administering reboxetine to a human being in need of treatment of reboxetine wherein the reboxetine is administered in a manner that results in 1) a first local maximum in reboxetine plasma concentration and 2) a second local maximum in reboxetine plasma concentration. The first local maximum will occur less than about 12 or less than about 10 hours prior to the second local maximum, such as about 2 hours to about 6 hours prior to the second local maximum. Normally, but not necessarily, the first local maximum in reboxetine plasma concentration and the second local maximum in reboxetine plasma concentration are the only maxima in reboxetine plasma concentration that occur within a single day.

Some embodiments include a dosage form comprising reboxetine, or manufacture of a dosage form comprising reboxetine, that, when administered orally, provides the first local maximum in reboxetine plasma concentration and the second local maximum in reboxetine plasma concentration, as described herein, to the human being to whom the dosage form has been administered.

These methods and dosage forms may be used to treat psychiatric or neurological disorders.

Some embodiments include a kit or product comprising one or more dosage forms comprising reboxetine described herein with a label that describes or instructs using the dosage forms as described herein to treat psychiatric or neurological disorders.

DETAILED DESCRIPTION

Unless otherwise indicated, any reference to a compound herein, such as reboxetine, by structure, name, or any other means, includes pharmaceutically acceptable salts; free acids or bases; alternate solid forms, such as polymorphs, solvates, hydrates, etc.; tautomers; enantiomers; deuterium modified compounds, such as deuterium modified reboxetine; or any chemical species that may rapidly convert to a compound described herein under conditions in which the compounds are used as described herein.

Reboxetine may be represented by the structure below, which is the mesylate salt.

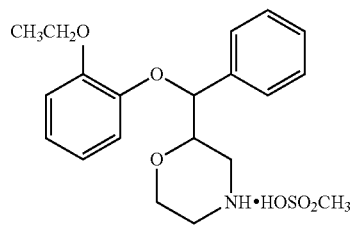

In some embodiments, reboxetine is in a salt form, a free base form, or may contain an excess (e.g., at least 60%, at least 70%, at least 80%, at least 90%, at least 95%, at least 97%, or at least 99%) of (+)-reboxetine or an excess (e.g., at least 60%, at least 70%, at least 80%, at least 90%, at least 95%, at least 97%, or at least 99%) (−)-reboxetine.

As mentioned above, for the methods described herein, the reboxetine is administered in a manner that results in 1) a first local maximum in reboxetine plasma concentration and 2) a second local maximum in reboxetine plasma concentration. For convenience, any method that results in a first local maximum in reboxetine and a second local maximum in reboxetine in a period substantially less than 12 hours, will be referred to as a "subject method."

In some embodiments, the first dosage form administered in a day, the only dosage form administered during the day, or the first of two dosage or more dosage forms administered during the day, is administered shortly after waking, such as within about 3 hours, within about 2 hours, within about 1.5 hours, within about 1 hour, within about 30 minutes, or within about 15 minutes of waking from an overnight sleep.

There are many potential ways that reboxetine could be administered in a manner that results in a first local maximum in reboxetine plasma concentration and a second local maximum in reboxetine plasma concentration. One method involves administering a single dosage form comprising a first release component and a second release component. Both the first release component and the second release component comprise reboxetine.

The first release component may release reboxetine, may begin releasing reboxetine, or may have a first local maximum in the plasma concentration of reboxetine, about 0-30 minutes, about 30-60 minutes, about 60-90 minutes, or about 90-120 minutes after the dosage form is orally administered, or any time period in a range bounded by any of these values. The second release component may release reboxetine after the first release component releases reboxetine, or may cause an increase of reboxetine plasma concentration or a second local maximum in the plasma concentration of reboxetine, that is about 1-10 hours, about 2-6 hours, about 1-2 hours, about 2-3 hours, about 3-4 hours, about 4-5 hours, about 5-6 hours, about 6-7 hours, about 1-3 hours, about 2-4 hours, about 3-5 hours, about 4-6 hours, about 5-7 hours, about 6-8 hours, or about 7-10 hours after reboxetine is first released from the first release component, or after the first local maximum in the plasma concentration of reboxetine, or at any time in a range bounded by any of these values.

The subject method may be carried out repeatedly for an extended period of time, e.g., at least 2 consecutive days, at least 7 consecutive days, at least 14 consecutive days, at least 28 consecutive days, at least 56 consecutive days, at least 60 consecutive days, or longer.

The first release component and the second release component may be incorporated into one single dosage form (such as a pill, tablet, capsule, caplet, or cachou). In one embodiment, the first release component would be located in one of the outer layers of the dosage form and the second release component would be located in one of the inner layers of the same dosage form.

In another embodiment, the first release component is located in a first layer of the dosage form, and the second release component is located in a second layer of the same dosage form. The two layers are distinct and may or may not be in contact with one another. In some embodiments, the two layers are stacked on top of one another and physically bound in a bi-layer structure (e.g., where the largest surfaces of the two layers contact one another, or the layers are thin compared to the other dimensions of the layers). In some embodiments, the two layers are positioned next to one another and physically bound in a bi-layer structure (e.g., where the layers are thicker than other dimensions of the layers).

In another embodiment, the first release component and the second release component may be constructed separately in their own specific granules, particles, or the like, wherein the first release component particles are formulated to release reboxetine before the second release component particles release reboxetine and wherein particles of both release profiles are combined together into a single dosage form, such as a capsule, pill, tablet, caplet, cachou or the like, and the two release components may or may not be physically bound to one another.

Another potential way to administer reboxetine in a manner that results in a first local maximum in reboxetine plasma concentration and a second local maximum in reboxetine plasma concentration is to administer a first dosage form containing reboxetine and, at a later time, a second dosage form containing reboxetine. The doses are administered at times that result in a first local maximum in reboxetine plasma concentration and a second local maximum in reboxetine plasma concentration. For example, the second dosage form may be administered less than half a day after the first dosage form, e.g., about 1-8 hours, about 8-12 hours, about 2-6 hours, about 2-3 hours, about 3-4 hours, about 4-5 hours, about 5-6 hours, about 6-7 hours, about 1-3 hours, about 2-4 hours, about 3-5 hours, about 4-6 hours, about 5-7 hours, about 6-8 hours, or about 740 hours, after the first dosage form, or any time period in a range bounded by any of these values.

In some embodiments, the first local maximum occurs about 1-30 minutes, about 30-60 minutes, about 1-2 hours, about 2-3 hours, or about 3-4 hours after the single dosage form or the first dosage form is administered, or at any time in a range bounded by, any of these values. Generally, the second local maximum occurs less than half a day after the first local maximum, such as about 140 hours, about 2-6 hours, about 2-3 hours, about 3-4 hours, about 4-5 hours, about 5-6 hours, about 6-7 hours, about 7-8 hours, about 1-3 hours, about 2-4 hours, about 3-5 hours, about 4-6 hours, about 5-7 hours, about 6-8 hours, or about 740 hours, after the first local maximum, or any time period in a range bounded by any of these values.

In some embodiments, two distinct maximum plasma concentrations are achieved by administering a first dosage form containing reboxetine and, at about the same time, a second dosage form containing reboxetine. In this example, the first dosage form and the second dosage form would be coated or formulated differently, such that the second local maximum (arising from the second dosage form) occurs less than half a day after the first local maximum (arising from the first dosage form), such as about 140 hours, about 2-6 hours, about 1-2 hours, about 2-3 hours, about 3-4 hours, about 4-5 hours, about 5-6 hours, about 6-7 hours, about 7-8 hours, about 1-3 hours, about 2-4 hours, about 3-5 hours, about 4-6 hours, about 5-7 hours, about 6-8 hours, or about 7-10 hours, after the first local maximum.

For dosage forms containing a first release component and a second release component, the first release component is associated with the first local maximum in reboxetine plasma concentration in that the first release component releases the reboxetine that contributes to the first local maximum in reboxetine plasma concentration. For example, the first release component could release reboxetine faster or sooner than the second release component, so that most of the reboxetine contributing to the first local maximum was released from the first release component.

For dosage forms containing a first release component and a second release component, the second release component is associated with the second local maximum in reboxetine plasma concentration in that the second release component releases the reboxetine that contributes to the second local maximum in reboxetine plasma concentration. For example, the second release component could delay release of its reboxetine so that at a time when the reboxetine plasma concentration is decreasing after the first local maximum, the second release component releases a sufficient amount of reboxetine to again increase the plasma concentration so that the second local maximum in reboxetine plasma concentration is achieved.

For dosage forms containing a first release component and a second release component, any suitable amount of reboxetine may be present in the first release component, such as about 1-10 mg, about 0.1-2 mg, about 0.5-1.5 mg, about 1-2 mg, about 1.5-2.5 mg, about 2-3 mg, about 2,5-3,5 mg, about 3-4 mg, about 3.5-4.5 mg, about 4-5 mg, about 4.5-5.5 mg, about 5-6 mg, about 6-7 mg, about 1-3 mg, about 2-4 mg, about 3-5 mg, about 4-6 mg, about 5-7 mg, about 7-10 mg, about 3-7 mg, about 4 mg, or any amount in a range bounded by any of these values.

For dosage forms containing a first release component and a second release component, any suitable amount of reboxetine may be present in the second release component, such as about 0.1-2 mg, about 0.5-1.5 mg, about 1-3 mg, about 1-2 mg, about 1.5-2.5 mg, about 2-3 mg, about 2.5-3.5 mg, about 3-4 mg, about 2-4 mg, about 3-5 mg, about 3.5-4.5 mg, about 4-5 mg, about 4.5-5.5 mg, about 4-6 mg, about 6-7 mg, about 5-7 mg, about 7-10 mg, about 3-7 mg, about 4 mg, or any amount in a range bounded by any of these values.

In some embodiments, the first release component provides immediate release of reboxetine. In some embodiments, the first release component provides delayed release of reboxetine. In some embodiments, the first release component provides sustained release of reboxetine.

In some embodiments, the second release component provides immediate release of reboxetine. In some embodiments, the second release component provides delayed release of reboxetine. In some embodiments, the second release component provides sustained release of reboxetine.

In some embodiments, the first release component provides immediate release of reboxetine, and the second release component provides delayed release of reboxetine. In some embodiments, the first release component provides immediate release of reboxetine, and the second release component provides sustained release of reboxetine.

With respect to methods wherein the reboxetine is administered in a first dosage form containing reboxetine and a second dosage form containing reboxetine, any suitable amount of reboxetine may be present in the first dosage form, such as about 140 mg, about 0.1-2 mg, about 0.5-4.5 mg, about 1-3 mg, about 1-2 mg, about 1.5-2.5 mg, about 2-3 mg, about 2.5-3.5 mg, about 3-4 mg, about 3.5-4.5 mg, about 4-5 mg, about 4.5-5.5 mg, about 5-6 mg, about 6-7 mg, about 2-4 mg, about 3-5 mg, about 4-6 mg, about 5-7 mg, about 740 mg, about 4 mg, or any amount in a range bounded by any of these values.

With respect to methods wherein the reboxetine is administered in a first dosage form containing reboxetine and a second dosage form containing reboxetine, any suitable amount of reboxetine may be present in the second dosage form, such as about 0,1-2 mg, about 0.5-1.5 mg, about 1-3 mg, about 1-2 mg, about 1.5-2.5 mg, about 2-3 mg, about 2.5-3.5 mg, about 3-4 mg, about 3.5-4.5 mg, about 4-5 mg, about 4.5-5.5 mg, about 5-6 mg, about 6-7 mg, about 2-4 mg, about 3-5 mg, about 4-6 mg, about 5-7 mg, about 7-10 mg, about 4 mg, or any amount in a range bounded by any of these values.

In some embodiments, the first dosage form provides immediate release of reboxetine. In some embodiments, the first dosage form provides delayed release of reboxetine. In some embodiments, the first dosage form provides sustained release of reboxetine.

In some embodiments, the second dosage form provides immediate release of reboxetine. In some embodiments, the second dosage form provides delayed release of reboxetine. In some embodiments, the second dosage form provides sustained release of reboxetine.

With respect to single dosage forms containing both a first release component and a second release component, in some embodiments, the dosage is administered within two hours of waking from an overnight sleep.

For some embodiments wherein more than one dosage form is given, the first dosage form may be administered within two hours of waking from an overnight sleep.

Controlled Release

There are many factors that can affect the overall time required for a drug substance such as reboxetine to be fully absorbed and/or reach a maximum plasma concentration in a human being. Among these factors is a human patient's age, weight, gender, level of stress, stomach contents, stomach pH level, and the presence of other medications. The time to maximum plasma concentration may also be affected by the time of day taken and the level of physical activity of the human patient. Another factor that can affect the time to maximum plasma concentration is the presence or absence of a controlled release coating.

Controlled release includes: immediate release of drug substance such as reboxetine at a certain time or in a certain area of the body; delayed release of a drug substance; sustained release of drug substance at a certain time or place in the body; or an extended release of a drug substance.

Reboxetine is normally rapidly absorbed in human patients, reaching a maximum plasma concentration in about 2-4 hours. To achieve a delay in the time required to reach a maximum plasma concentration, a controlled release coating or mixture may be employed.

Delayed release is a general drug delivery term that describes the form of an oral medication that does not immediately discharge its active drug component in the mouth or in the stomach of a patient. While there may be many ways to achieve delayed release, delayed release may be achieved by completely or partially surrounding the reboxetine, e.g., in the second release component with a coating or layer (e.g., an inner controlled release coating) that does not immediately dissolve when swallowed. For example, the material of the coating or layer may slowly dissolve in the stomach, and/or slowly disintegrate by chemical reaction, such as by hydrolysis, in the stomach until the layer can no longer prevent the reboxetine from coming into contact with the gastric fluid.

In some embodiments, the delayed release coating ensures delivery through the stomach and into the intestines. Once in the duodenum, the coating may begin to break down and begin to release reboxetine. In some cases, the reboxetine may be completely released in the duodenum. In some embodiments, the reboxetine may be partially released in the duodenum, and partially released in the jejunum. In some cases, the reboxetine may be completely released in the jejunum. In some cases, the reboxetine may be partially released in the jejunum and partially released in the ilium. In some cases, the reboxetine may be completely released in the ilium. In some cases, the reboxetine may be partially released in the duodenum, the jejunum, and the ilium. In some embodiments, the reboxetine may be partially released in the ilium, and partially released in the colon, In some cases, the reboxetine may be completely released in the colon.

The time of the delayed release, e.g., between release of the first reboxetine component and the second reboxetine component, can be adjusted by using a material that dissolves or disintegrates more or less slowly in the digestive system, adjusting the thickness of the layer or coating (e.g., a thicker layer would provide a longer time), and/or by using materials whose properties are sensitive to pH. For example, materials that are less stable to, or more soluble in, acidic pHs, may dissolve or disintegrate more quickly in the stomach because the stomach pH is lower than the pH in the intestines. Conversely, materials that are stable at low pH, but less stable at higher pH may dissolve or disintegrate later because of the time it takes the dosage form to travel through the gastrointestinal tract.

A controlled release formulation containing reboxetine can be coated with one or more functional or non-functional coatings. Examples of functional coatings include controlled release polymeric coatings (i.e., controlled release coats), moisture barrier coatings, enteric polymeric coatings, and the like.

A controlled release polymer may be used for both sustained release or for delayed release, depending upon the structure of the dosage form. For example, interspersing the reboxetine throughout a controlled release polymer can provide sustained release, since the drug will be released for as long as the polymer is present in the GI tract. Delayed release may be achieved by creating a barrier, such as a coating, which is intended to last for a shorter time (e.g., less than 12 hours, less than 10 hours, less than 6 hours, less than 3 hours, etc.), so that when the barrier is penetrated, the reboxetine is freely released. The thickness of the barrier can be used to control the delay time.

Any suitable controlled release polymer may be used, such as acrylic acid and methacrylic acid copolymers and various esters thereof, e.g., methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polyacrylamide, poly(methacrylic acid anhydride), and glycidyl methacrylate copolymers.

Other suitable controlled release polymers include polymerizable quaternary ammonium compounds, e.g., quaternized aminoalkyl esters and aminoalkyl amides of acrylic acid and methacrylic acid, for example (β-methacryloxyethyltrimethylammonium methosulfate, β-acryloxypropyltrimethylammonium chloride, and trimethylaminomethylmethacrylamide methosulfate. The quaternary ammonium atom can also be part of a heterocycle, as in methacryloxyethylmethylmorpholinium chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryltrialkyl ammonium salts, and the like. Other polymerizable quaternary ammonium compounds benzyldimethylarnmoniurnethylmethacrylate chloride, diethylmethylammoniumethyl-acrylate and -methacrylate methosulfate, N-trimethylammoniumpropylmethacrylamide chloride, and N-trimethylammonium-2,2-dimethylpropyl-1-methacrylate chloride.

Delayed release may also achieved by using a controlled release polymer that targets a particular pH, with the understanding that, with proper fasting or feeding, the pH could correspond to a particular time after administration.

For some controlled release polymers, an acrylic or methacrylic polymer comprises one or more ammonio methacrylate copolymers. Ammonio methacrylate copolymers (such as those sod by Evonik under the trademark EUDRAGIT® RS and RL) are fully polymerized copolymers of acrylic and methacrylic acid esters with a low content of quaternary ammonium groups. The ammonium groups are appended to the ester portion of the methacrylate (as 2-trimethylammonium-ethyl esters). The charged ammonium groups in these polymers make them insoluble and highly permeable with pH-independent swelling. These properties make these polymers useful for customized, time-controlled release of the coated drug. In order to obtain a desirable dissolution profile for a given therapeutically active agent, such as reboxetine, two or more ammonio methacrylate copolymers having differing physical properties can be incorporated. For example, it is known that by changing the molar ratio of the pre-polymerized materials containing quaternary ammonium groups to pre-polymerized materials containing the uncharged, neutral methacrylic or acrylic esters, the permeability properties of the resultant coating can be modified.

In other embodiments, the control releasing coat further includes a polymer whose permeability is pH dependent, such as anionic polymers synthesized from methacrylic add and methacrylic acid methyl ester. Such polymers are commercially available, e.g., from Evonik, under the tradename EUDRAGIT® L and EUDRAGIT® S. The ratio of free carboxyl groups to the esters is known to be 1:1 in EUDRAGIT® L and 1:2 in EUDRAGIT® S. EUDRAGIT® L is insoluble in acids and pure water, but becomes increasingly permeable above pH 5.0. This makes EUDRAGIT® L appropriate for targeting release of the coated drug substance such as reboxetine in the duodenum and the jejunum of the small intestine. Thus, a EUDRAGIT® L coated drug substance may achieve a delay in maximum plasma concentration, relative to an uncoated or immediate release drug substance (e.g., reboxetine in a first release component), of about 30 min to about 1 hour, about 1-1.5 hours, about 1.5-2 hours, about 2-2.5 hours, about 2.5-3 hours, or about 3.5-4 hours.

EUDRAGIT® S is similar to EUDRAGIT® L, except that it becomes increasingly permeable above pH 7. This makes EUDRAGIT® S appropriate for targeting release of the coated drug substance such as reboxetine in the ileum of the small intestine and also the colon. Thus, a EUDRAGIT® S coated drug substance may achieve a delay in maximum plasma concentration, relative to an uncoated or immediate release drug substance (e.g., reboxetine in a first release component), of about 1-2 hours, about 2-3 hours, about 3-4 hours about 4-5 hours, about 5-6 hours, about 6-7 hours, about 7-8 hours, about 8-9 hours, or about 9-10 hours.

A hydrophobic acrylic polymer coating can also include a polymer which is based on dimethylaminoethyl methacrylate and neutral methacrylic acid esters (such as EUDRAGIT® F, commercially available from Evonik). EUDRAGIT® E is not soluble in saliva (making it useful for taste and odor masking) but is soluble in gastric fluid up to pH 5 which provides an immediate release of drug product in the stomach. Reboxetine surrounded with a EUDRAGIT® E coating may release reboxetine, may begin releasing reboxetine, or may have a first local maximum in the plasma concentration of reboxetine, at a time of about 0-30 minutes, 30-60 minutes, 60-90 minutes, or 90-120 minutes after the dosage form is orally administered, or any time period in a range bounded by any of these values.

A hydrophobic acrylic polymer coating can include a neutral copolymer based on a poly methacrylate, such as EUDRAGIT® NE (NE=neutral ester), commercially available from Evonik. EUDRAGIT® NE 30D lacquer films are insoluble in water and digestive fluids, but permeable and swellable, providing another option for time-controlled release. EUDRAGIT® NE has a pH-independent sustained release effect that can release a drug substance such as reboxetine over a period of time, or may delay release fora period of time, wherein the time of release or delay is about 1-24 hours, about 148 hours, about 142 hours, about 1-8 hours, or about 1-6 hours.

In some embodiments, the control releasing coat comprises a polymer comprising ethyl acrylate and methyl methacrylate in a 2:1 ratio (KOLLICOAT® EMM 30 D, BASF). KOLLICOAT® EMM 30 D has a pH-independent sustained release effect that can release a drug substance such as reboxetine over a period of time, or may delay release for a period of time, wherein the time of release or delay is about 1-24 hours, about 1-18 hours, about 1-12 hours, about 1-8 hours, or about 1-6 hours.

In some embodiments, the control releasing coat comprises a polyvinyl acetate stabilized with polyvinylpyrrolidone and sodium lauryl sulfate such as KOLLICOAT® SR30D (BASF). The dissolution profile can by altered by changing the relative amounts of different acrylic resin lacquers included in the coating. Also, by changing the molar ratio of polymerizable permeability-enhancing agent (e.g., the quaternary ammonium compounds) to the neutral methacrylic esters, the permeability properties (and thus the dissolution profile) of the resultant coating can be modified. KOLLICOAT® SR30D is another coating with a pH-independent sustained release effect that can release a drug substance such as reboxetine over a period of time, or may delay release for a period of time, wherein the time of release or delay is about 1-24 hours, about 1-18 hours, about 1-12 hours, about 1-8 hours.

In some embodiments, the control releasing coat comprises ethylcellulose, which can be used as a dry polymer (such as ETHOCEL™, Dow Chemical Company) solubilized in organic solvent prior to use, or as an aqueous dispersion. One suitable commercially-available aqueous dispersion of ethylcellulose is Aquacoat® (Danisco). Aquacoat® ECD (ethylcellulose aqueous dispersion) Aquacoat® ARC (alcohol-resistant ethylcellulose aqueous dispersion) Aquacoat® CPD (cellulose acetate phthalate aqueous dispersion) are all commercially available controlled release coatings. Another suitable aqueous dispersion of ethylcellulose is commercially available as Surelease® (Colorcon, Inc.). This product can be prepared by incorporating plasticizer into the dispersion during the manufacturing process. A hot melt of a polymer, plasticizer (e.g., dibutyl sebacate), and stabilizer (e.g., oleic acid) is prepared as a homogeneous mixture, which is then diluted with an alkaline solution to obtain an aqueous dispersion which can be applied directly onto substrates. These coatings have a pH-independent sustained release effect that can release a drug substance such as reboxetine over a period of time, or may delay release for a period of time, wherein the time of release or delay is about 1-24 hours, about 148 hours, about 1-12 hours, about 1-8 hours, about 1-6 hours, about 1-4 hours, or about 1-2 hours.

Other examples of polymers that can be used in the control-releasing coat include cellulose acetate phthalate, cellulose acetate trimaleate, hydroxypropyl methylcellulose phthalate, hydroxypropyl methylcellulose acetate succinate, polyvinyl alcohol phthalate, shellac, hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight 5 k to 5000 k), polyvinylpyrrolidone (molecular weight 10 k to 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight 30 k to 300 k), polysaccharides such as agar, acacia, karaya, tragacanth, algins and guar, polyacrylamides, POLYOX® polyethylene oxides (molecular weight 100 to 5000 k, Dow), AQUA KEEP® acrylate polymers (composed of mainly acrylic acid polymer, sodium salt), diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic add, natural gums, lecithins, pectin, alginates, ammonia alginate, sodium, calcium, potassium alginates, propylene glycol alginate, agar, and gums such as arabic, karaya, locust bean, tragacanth, carrageenan, guar, xanthan, scleroglucan and mixtures and blends thereof.

In some embodiments, the dosage forms of reboxetine are coated with polymers in order to facilitate mucoadhesion within the gastrointestinal tract. Non-limiting examples of polymers that can be used for mucoadhesion include carboxymethylcellulose, polyacrylic acid, Carbopol™ (Lubrizol), polycarbophil, gelatin and other natural or synthetic polymers.

The polymeric coatings of the present disclosure may be any one of the described coatings or may be a combination of two or more of the described coatings to achieve the desired release profiles of the release of reboxetine.

In addition to the modified release dosage forms described herein, other modified release technologies known to those skilled in the art can be used in order to achieve the modified release formulations of the present disclosure, i.e., formulations which provide a mean $T_{max}$ of the drug and/or other pharmacokinetic parameters described herein when administered e.g., orally or by other mode of administration to human patients. Such formulations can be manufactured as a modified release oral formulation in a suitable tablet or multiparticulate formulation known to those skilled in the art. In either case, the modified release dosage form can optionally include a controlled release carrier which is incorporated into a matrix along with the drug, or which is applied as a controlled release coating.

Any dosage form comprising an effective amount of reboxetine may further comprise a binder, a lubricant, and other conventional inert excipients.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the tablets is in the form of a solution binder. Non-limiting examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (e.g., hydroxypropyl methylcellulose (HPMC) and hydroxypropyl cellulose (HPC)), polyvinyl alcohol and mixtures thereof. Any suitable amount of binder may be present, such as about 0.5-5%, about 540%, about 10-15%. about 15-20%, about 20-25%, about 0.5-25%, about 0.5-15%, about 1-6%, or about 3% by weight of the tablet dry weight. In some embodiments, the binder is polyvinyl alcohol.

Lubricants can be added to pharmaceutical formulations to decrease any friction that occurs between the solid and the die wall during tablet manufacturing. High friction during tableting can cause a series of problems, including inadequate tablet quality (capping or even fragmentation of tablets during ejection, and vertical scratches on tablet edges) and may even stop production. Accordingly, lubricants may be added to tablet formulations. Non-limiting examples of lubricants useful for the core include glyceryl behenate, stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K), stearyl alcohol, leucine, polyethylene glycol (MW 1450, suitably 4000, and higher), magnesium stearate, glyceryl monostearate, stearic acid, polyethylene glycol, ethylene oxide polymers (for example, available under the registered trademark CARBOWAV) from Union Carbide, Inc., Danbury, Conn.), sodium lauryl sulfate, magnesium lauryl sulfate, sodium oleate, sodium stearyl fumarate, DL-leucine, colloidal silica, mixtures thereof and others as known in the art. In some embodiments, the lubricant is glyceryl behenate (for example, COMPRITOL® 888). Any suitable amount of binder may be present, such as about 0.5-5%, about 540%, about :1045%, about 15-20%, about 20-25%, about 0.5-25%, about 0.5-15%, about 1-6%, or about 3% by weight of the tablet dry weight.

Dosage Forms (A) Multi-Layer Single Dosage Form Having 2 Release Components in a Layered Core Configuration One specific aspect of the present disclosure comprises a controlled release dosage form having an inner layer, or a core, comprising reboxetine and conventional excipients. In some embodiments, the core of the dosage form can be surrounded by a controlled release coat, which delays or sustains the release of the reboxetine. The dosage form may comprise one or more additional functional or non-functional coats surrounding the core or controlled release coat. In at least one embodiment, the core's controlled release coat is surrounded by at least one coating containing reboxetine. The outer reboxetine layer or coating may be further surrounded by, an immediate release coating or another controlled release coating. The controlled release single dosage form may be a pill, tablet, capsule, caplet, or cachou.

The multi-layer single dosage form comprises, in total, an effective amount of reboxetine that is about 2-12 mg, about 2-4 mg, about 3-5 mg, about 4-6 mg, about 5-7 mg, about 6-8 mg, about 7-9 mg, about 8-10 mg, about 9-11 mg, about 10-12 mg, 12-16 mg, or about 8 mg.

The amount of the reboxetine present in the core of a multi-layer single dosage form can vary in an amount from about 0.01% to about 90% by weight of the total dry weight of the single dosage form. For example, in certain embodiments the amount of reboxetine is present in the core of a multi-layer single dosage form in an amount from about 1-10%, about 10-20%, about 20-30%, about 30-40%, about 40-50%, about 50-60%, about 60-70%, about 70-80%, about 80-90%, about 40-60%, about 0.01-5%, about 5-10%, about 10-15%, about 15-20%, about 20-25%, about 25-30%, about 30-35%, about 35-40%, about 40-45%, about 45-50%, about 50-55%, about 55-60%, about 40%, about 45%, or about 50% of the total dry weight of the multi-layer single dosage form. For example, in certain embodiments, the core comprises about 0.54 mg, about 1-2 mg, about 2-3 mg, about 3-4 mg, about 4-5 mg, about 5-6 mg, about 6-7 mg, about 7-8 mg, about 8-9 mg, about 2 mg, about 3 mg, about 4 mg, about 5 mg, about 6 mg, about 7 mg, or about 8 mg of reboxetine.

The core of the multi-layer single dosage form comprises an effective amount of reboxetine and may further comprise a binder, a lubricant, and other conventional inert excipients.

For some multi-layer dosage forms, the core may be surrounded by any of the controlled release polymers described above. In other embodiments, the core of the multi-layer single dosage form may be dispersed in any of the controlled release polymers described above. For example, in one embodiment, the core is surrounded by a delayed release coating. In some examples, the delayed release coating comprises EUDRAGIT® S. The delayed release coating of the core may result in a delay of the release of the reboxetine of the core of about 1-2 hours, about 2-3 hours, about 3-4 hours about 4-5 hours, about 5-6 hours, about 6-7 hours, about 7-8 hours, about 8-9 hours, or about 9-10 hours. In other embodiments, the core is surrounded by a sustained release coating. In another example, the core is surrounded by or dispersed in a coating comprising KOLLICOAT® EMM 30 D. The sustained release coating (or dispersion) of the core may result in a prolonged release of the reboxetine of the core over about 1-2 hours, about 1-3 hours, about 1-4 hours, about 1-5 hours, about 1-6 hours, about 1-7 hours, about 1-8 hours, about 1-9 hours about 140 hours, about 1-11 hours, about 1-12 hours, about 1-13 hours, about 1-14 hours, about 1-15 hours, about 1-16 hours, or about 2 hours, about 3 hours, about 4 hours, about 5 hours, about 6 hours, about 7 hours, about 8 hours, about 9 hours, or about 10 hours.

Any of the controlled release reboxetine cores described herein may be coated with additional outer layers, at least one of which comprises reboxetine. In some cases, the outer layer containing reboxetine may be optionally surrounded by a controlled release coating or another functional or non-functional coating. In other embodiments, the outer layer containing reboxetine may be optionally dispersed throughout a controlled or sustained release polymer or another functional release coating. The outer layer containing reboxetine may contain an amount of reboxetine less than, equal to, or greater than the amount of reboxetine contained in the inner core structure. The outer layer of the controlled release multi-layer single dosage form may comprise an effective amount of reboxetine, a binder, a lubricant and can contain other conventional inert excipients.

The amount of the reboxetine present in the outer layer of a multi-layer single dosage form can vary in an amount from about 0.01% to about 90% by weight of the dry weight of the single dosage form. For example, in certain embodiments reboxetine in the outer layer is present in an amount from 40% to 60% by weight of the single dosage form's dry weight. For example, in certain embodiments, the outer layer of the multi-layer single dosage form of the present disclosure comprises reboxetine in a proportion of about 1-10%, about :10-20%, about 20-30%, about 30-40%, about 40-50%, about 50-60%, about 60-70%, about 70-80%, about 80-90%, about 30%, about 0.01-5%, about 540%, about 1045%, about 15-20% about 20-25%, about 25-30%, about 30-35%, about 35-40%, about 40-45%, about 45-50%, about 50-55%, about 55-60%, about 60-65% about 65-70%, about 45%, about 50%, or about 55% of the total dry weight of the multi-layer single dosage form. For example, in certain embodiments, the outer layer comprises about 0.54 mg, about 1-2 mg, about 2-3 mg, about 3-4 mg, about 4-5 mg, about 5-6 mg, about 6-7 mg, about 7-8 mg, about 8-9 mg, about 2 mg, about 3 mg, about 4 mg, about 5 mg, about 6 mg, about 7 mg, or about 8 mg of reboxetine.

For some multi-layer single dosage forms, the outer reboxetine layer may be surrounded by any of the controlled release polymers described above. In other embodiments, the outer reboxetine layer of the multi-layer single dosage form may be dispersed in any of the controlled release polymers described above. For example, in one embodiment, the outer reboxetine layer is surrounded by an immediate release coating. In some examples, the immediate release coating comprises EUDRAGIT® E. The immediate release coating of the outer reboxetine layer may result in the complete release of the reboxetine of the outer reboxetine layer in about 1-5 minutes, about 5-10 minutes, about 10-15 minutes, about 15-20 minutes, about 20-25 minutes, about 25-30 minutes, about 30-60 minutes, about 60-90 minutes, or about 90-120 minutes. In other embodiments, the outer reboxetine layer is surrounded by or dispersed in a sustained release coating. In another example, the outer reboxetine layer is surrounded by or dispersed in a polymer comprising polyvinylpyrrolidone and/or cellulose derivatives. The polymer coating (or dispersion) of the core may result in a release of the reboxetine of the core over about 1-5 minutes, about 5-10 minutes, about 10-15 minutes, about 15-20 minutes, about 20-25 minutes, about 25-30 minutes, about 30-60 minutes, about 60-90 minutes, or about 90-120 minutes.

In at least one embodiment, a multi-layer single dosage form contains a total amount of reboxetine that is about 0.1-16 mg, such as about 0.1-1 mg, about 1-2 mg, about 2-3 mg, about 3-4 mg, about 5-6 mg, about 6-7 mg, about 7-8 mg, about 8-9 mg, about 9-10 mg about 10-11 mg, about 11-12 mg, about 12-13 mg, about 13-14 mg, about 14-15 mg, about 15-16 mg, about 0.1-5 mg, about 5-10 mg, about 10-16 mg, about 2-6 mg, about 6-10 mg, or about 7-9 mg. In some embodiments, the reboxetine is present at from 0.1-85% by weight of the dry weight of the multi-layer single dosage form, such as about 0.1-5%, about 5-10%, about 10-15%, about 15-20%, about 20-30%, about 30-40%, about 40-50%, about 50-70%, or about 70-90%. In embodiments wherein reboxetine is present in both an outer layer and an inner core layer, it is understood that the release of the outer layer of reboxetine precedes the release of the inner layer or core of reboxetine. Thus, the first pulse of reboxetine k from the outer layer followed at a later time by the second puke of reboxetine from the inner layer or core.

In other embodiments, a moisture barrier can optionally be added to surround the outermost controlled release coat. If present, this moisture barrier may affect in vitro drug release as well as precluding moisture from coming into contact with the reboxetine.

In one embodiment, the outer layer containing reboxetine is an immediate release formulation of reboxetine.

In one embodiment, the inner core containing reboxetine is a coated with a controlled release layer wherein the reboxetine is released 2-6 hours after the initial release outer layer.

In another aspect, the single dosage form is administered within two hours after waking from an overnight sleep.

(B) Bi-Layer Single Dosage Form Having 2 Release Components in a Layer-On-Layer Configuration In another specific feature of the present disclosure, two or more layers containing reboxetine may be incorporated in a single dosage form, wherein the layers are physically bound to one another. In some embodiments, the layers are positioned on top of one another. In other embodiments, the layers are positioned side-by-side. In some cases, the bi-layer single dosage form may be a pill, tablet, capsule, caplet, or cachou. Bi-layer tablets are a dosage form of particular interest.

In some examples, the first layer of a hi-layer single dosage form has the composition and properties described above for the outer reboxetine layer, and its coating layer, of the multi-layer single dosage form described above in part (A). In some cases, the second layer of a bi-layer single dosage form has the composition and properties described above for the inner (or core) reboxetine layer, and its coating layer, of the multi-layer single dosage form described above in part (A). In at least one embodiment, the first layer of the bi-layer single dosage form corresponds to the first reboxetine release component, and the second layer of the bi-layer single dosage form corresponds to the second reboxetine release component, both of which are described in detail above.

In embodiments wherein reboxetine is present in both a first layer and a second layer, it is understood that the release of reboxetine from the first layer precedes the release of the reboxetine from the second layer. Thus, the first pulse of reboxetine is from the first layer, followed at a later time by the second pulse of reboxetine from the second layer.

In one embodiment, the first layer of a bi-layer single dosage form containing reboxetine is surrounded by an immediate release coating layer.

In another embodiment, the second layer of a bi-layer single dosage form containing reboxetine is coated with, or dispersed in, a controlled release layer wherein the reboxetine is released 2-6 hours after the release of the reboxetine from the first layer.

In some embodiments, the entire multi-layer dosage form is surrounded by an immediate release coating layer, with the understanding that the second layer of the bi-layer dosage form is coated with, or dispersed in, a controlled release layer wherein the reboxetine of the second layer is released 2-6 hours after the release of the reboxetine from the first layer.

In another example, the bi-layer single dosage form is administered within two hours after waking from an overnight sleep.

(C) Multi-Particle Single Dosage Form Having 2 Release Components

In another specific aspect of the present disclosure, two or more varieties of a controlled release core particle are incorporated into a single formulation wherein the two or more particle varieties are not physically attached to one another. In this aspect, the two or more particle types are contained within a single structure which may or may not be surrounded by a control releasing coating. This structure may be in the form of a capsule, a caplet, a tablet, a cachou, or the like.

In some examples, the first particle component of the multi-particle single dosage form has the composition and properties described above for the outer reboxetine layer, and its coating layer, of the multi-layer single dosage form described above in part (A). In some cases, the second particle component of the multi-particle single dosage form has the composition and properties described above for the inner (or core) reboxetine layer, and its coating layer, of the multi-layer single dosage form described above in part (A). In at least one embodiment, the first particle component of the multi-particle single dosage form corresponds to the first release component, and the second particle component of the multi-particle single dosage form corresponds to the second release component.

In embodiments wherein reboxetine is present in both a first particle component and a second particle component, it is understood that the release of reboxetine from the first particle component precedes the release of the reboxetine from the second particle component. Ties, the first pulse of reboxetine is from the first particle component, followed at a later time by the second pulse of reboxetine from the second particle component.

In one embodiment, the first particle component of a multi-particle single dosage form containing reboxetine is surrounded by an immediate release coating layer.

In some embodiments, the second particle component of a multi-particle single dosage form containing reboxetine is coated with a controlled release layer wherein the reboxetine is released 2-6 hours after the release of the reboxetine from the first particle component.

In some examples, the multi-particle single dosage form is administered within two hours after waking from an overnight sleep.

(D) First Dosage Form and Second Dosage Form Administered at Specific Time Intervals Another specific aspect of the present disclosure is the administration of two or more controlled release dosage forms at specific time intervals. The two or more controlled release dosage forms may be identical in composition, comprising a core of reboxetine and conventional excipients. The core can be surrounded by a controlled release coat that may provide immediate release, delayed release, sustained release, or extended release of the reboxetine. This dosage may be in the form of a capsule, a caplet, a tablet, a cachou, or the like.

In some examples, the reboxetine is delivered in a controlled release dosage form, such as tablet, comprising; (i) a core that includes reboxetine (e.g. from 40% to 99% by weight of tablet dry weight), a binder such as polyvinyl alcohol (e.g. from 0.5% to 25% by weight of tablet dry weight), and a lubricant such as glyceryl behenate (e.g. from 0.1% to 5% by weight of tablet dry weight); and (ii) a control releasing coat that includes a water-insoluble water-permeable film-forming polymer such as ethylcellulose (e.g. from 1% to 12% by weight of tablet dry weight), a water-soluble polymer such as polyvinylpyrrolidone, (e.g. from 1.5% to 10% by weight of tablet dry weight), optionally a plasticizer such as dibutyl sebacate, polyethylene glycol 4000 or a mixture thereof (e.g. from 0,5% to 4% by weight of tablet dry weight), and optionally a wax such as carnauba wax (e.g. from 0.01% to 0.05% by weight of tablet dry weight).

In at least one embodiment of the disclosure, the dosage form is a 5 mg tablet comprising: (i) a core that includes reboxetine (e.g., 80% by weight of tablet dry weight), a binder such as polyvinyl alcohol (e.g. 3% by weight of tablet dry weight), and a lubricant such as glyceryl behenate (e.g. 3% by weight of tablet dry weight); and (ii) a control releasing coat that includes a water-insoluble water-permeable film-forming polymer such as ethylcellulose (e.g. 6% by weight of tablet dry weight), a water-soluble polymer such as polyvinylpyrrolidone (e.g. 5% by weight of tablet dry weight), optionally a plasticizer such as dibutyl sebacate, polyethylene glycol 4000 or a mixture thereof (e.g. 3% by weight of tablet dry weight), and optionally a wax such as carnauba wax (e.g. 0.03% by weight of tablet dry weight).

In some embodiments, the core formulation is an uncoated immediate release formulation resulting in 100% dissolution of the reboxetine within 1 hour, within 45 minutes, within 30 minutes, within 15 minutes, within 10 minutes, within 5 minutes, or within 1 minute. In at least one embodiment, the core is a normal release matrix formulation. In certain embodiments, the core comprises an effective pharmaceutical amount of reboxetine, a binder (e.g., polyvinyl alcohol), and a lubricant (e.g., glyceryl behenate). Additional inert excipients can also be added to the core formulation. The additional inert excipients can be added to facilitate the preparation and/or improve patient acceptability of the final extended-release dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In some embodiments, the controlled release dosage form has the composition and properties described above for the outer reboxetine layer of the multi-layer single dosage form described above in part (A). In some cases, the controlled release dosage form has the composition and properties described above for the inner (or core) reboxetine layer of the multi-layer single dosage form described above in part (A). Typically, the first controlled release dosage form corresponds to the first reboxetine release component, and the second controlled release dosage form corresponds to the second reboxetine release component.

It is generally understood that the release of reboxetine from the first controlled release dosage form precedes the release of the reboxetine from the second controlled release dosage form. Therefore, the first maximum plasma concentration of reboxetine is from the first controlled release dosage form, followed at a later time by the second maximum plasma concentration of reboxetine from the second controlled release dosage form.

In some embodiments, the administration of the first controlled release dosage form is administered about 2 hours to about 8 hours before the administration of the second controlled release dosage form. In additional embodiments, the second controlled release dosage form is administered about 2-3 hours, about 3-4 hours, about 4-5 hours, about 5-6 hours, about 6-7 hours, about 7-8 hours, about 4 hours, about 5 hours, or about 6 hours after administration of the first controlled release dosage form.

In one embodiment, the first controlled release single dosage form containing reboxetine is surrounded by an immediate release coating layer.

In some embodiments, the first controlled release single dosage form containing reboxetine is coated with a controlled release layer wherein the reboxetine is released 1-6 hours after administration.

In some cases, the first controlled release single dosage form is administered within two hours after waking from an overnight sleep.

(E) First Dosage Form and Second Dosage Form Administered at the Same Time

In another embodiment of the present disclosure, two or more non-identical controlled release dosage forms are administered at about the same time. The two or more controlled release dosage forms each comprise a core of reboxetine and conventional excipients, as described above in part (D). In one embodiment, the two or more dosage forms comprise differing controlled release coatings, analogous to the core and the outer layer as described above in part (A). In one example, a first dosage form of reboxetine is uncoated, or is surrounded by an immediate release coating, and a second dosage form is surrounded by a delayed, sustained, or extended release coating. Both dosage forms may be in the form of a capsule, a caplet, a tablet, a cachou, or the like.

In some embodiments, the first controlled release dosage form has the composition and properties described above for the outer reboxetine layer of the multi-layer single dosage form described above in part (A). In some cases, the controlled release dosage form has the composition and properties described above for the inner (or core) reboxetine layer of the multi-layer single dosage form described above in part (A). Typically, the first controlled release dosage form has the composition and properties of the first reboxetine release component, and the second controlled release dosage form has the composition and properties of the second reboxetine release component. In one example, the first controlled release dosage form containing reboxetine is surrounded by an immediate release coating layer.

In some cases, the second controlled release dosage form containing reboxetine is coated with a controlled release layer wherein the reboxetine is released 2-6 hours after the release of the reboxetine from the first controlled release dosage form.

In some embodiments, a first local maximum provided by the first controlled release dosage form occurs about 2 hours to about 6 hours prior to the second local maximum provided by the second controlled release dosage form.

In some examples, the first controlled release single dosage form is administered within two hours after waking from an overnight sleep.

(F) Other Delivery Methods

Other controlled release drug formulations are optionally contemplated in the present disclosure. In some embodiments, reboxetine is administered in both a long-term controlled release manner (by the use of a patch or similar dermal adhesive drug delivery device) and also a daily treatment manner. In some examples, reboxetine is delivered to a patient in the form of an implanted device. In this particular embodiment, reboxetine may be incorporated into a slowly degrading polymer to release the drug slowly over time. The time period for complete degradation and release of drugs from such an implant may be 1-4 weeks, 4-6 weeks, 6-8 weeks, 8-12 weeks, 12-16 weeks, 16-18 weeks, 2-6 months, 6-12 months, or any time period in a range bounded by any of these values. Reboxetine may be incorporated into another polymeric implant device wherein the reboxetine is released in a pulse-like manner from individual wells in the polymeric device. In this embodiment, the wells containing drug are coated with controlled release membranes that release drug in distinctly timed pulses. These membranes would be constructed of the controlled release coating described herein. The device containing the wells may itself degrade over time. The time period for complete release of drugs from such an implant may be 1-4 weeks, 4-6 weeks, 6-8 weeks, 8-12 weeks, 12-16 weeks, 16-18 weeks, 2-6 months, 6-12 months, or any time period in a range bounded by any of these values.

It is envisioned that the amount of drug delivered from the devices above would provide a low steady state concentration of reboxetine which would fall below the maximum plasma concentration associated with a dosage forms described herein. While the reboxetine is administered chronically by a long-term controlled release device, it is envisioned that reboxetine may also be administered in a daily dose of one of the above formulations described in part (D).

The reboxetine may be provided to the blood of a human being for treating psychiatric or neurological disorders, such as depression, including major depressive disorder or treatment-resistant depression, and narcolepsy, including narcolepsy with cataplexy and/or excessive daytime sleepiness.

The following embodiments are specifically contemplated.

EMBODIMENTS

Embodiment 1

A method of providing reboxetine to the blood of a human being comprising: administering reboxetine to a human being in need of treatment with reboxetine in a manner that results in:
1) a first local maximum in reboxetine plasma concentration, and
2) a second local maximum in reboxetine plasma concentration;
wherein the first local maximum occurs about 2 hours to about 6 hours prior to the second local maximum.

Embodiment 2

The method of embodiment 1, wherein the reboxetine is administered in a single dosage form that provides both: 1) the first local maximum in reboxetine plasma concentration and 2) the second local maximum in reboxetine plasma concentration, wherein the single dosage form is administered within two hours after waking from an overnight sleep.

Embodiment 3

The method of embodiment 2, wherein the single dosage form is a single pill, tablet, capsule, caplet, or cachou.

Embodiment 4

The method of embodiment 2 or 3, wherein the single dosage form comprises an inner core containing reboxetine and an outer coating layer containing reboxetine.

Embodiment 5

The method of embodiment 4, wherein an inner controlled release coating is disposed between the inner core containing reboxetine and the outer coating layer containing reboxetine.

Embodiment 6

The method of embodiment 5, wherein the inner controlled release coating provides delayed release of the inner core containing reboxetine.

Embodiment 7

The method of embodiment 5 or 6, wherein the outer coating layer comprising reboxetine is further surrounded by an outer controlled release layer.

Embodiment 8

The method of embodiment 7, wherein the outer controlled release layer provides delayed release of the outer coating layer containing reboxetine.

Embodiment 9

The method of embodiment 7, wherein the outer controlled release layer provides immediate release of the outer coating layer containing reboxetine.

Embodiment 10

The method of embodiment 2 or 3, wherein the single dosage form comprises reboxetine in a first controlled release layer and a second controlled release layer, wherein the controlled release layers are physically bound to one another in a bi-layer structure.

Embodiment 11

The method of embodiment 10, wherein the first controlled release layer is coated with a first controlled release coating, and the second controlled release layer is coated with a second controlled release coating.

Embodiment 12

The method of embodiment 11, wherein the first controlled release coating provides immediate release of the first controlled release layer.

Embodiment 13

The method of embodiment 11 or 12, wherein the second controlled release coating provides delayed release of the second controlled release layer.

Embodiment 14

The method of embodiment 2 or 3, wherein the single dosage form comprises reboxetine in a first controlled release component and a second controlled release component, wherein the controlled release components are not physically bound to one another.

Embodiment 15

The method of embodiment 14, wherein the first controlled release component provides immediate release of reboxetine.

Embodiment 16

The method of embodiment 14 or 15, wherein the second controlled release component provides delayed release of reboxetine.

Embodiment 17

The method of embodiment 1, wherein the reboxetine is administered in a first dosage form that provides: 1) the first local maximum in reboxetine plasma concentration; and a second dosage form that provides: 2) the second local maximum in reboxetine plasma concentration; wherein the first dosage form is administered within two hours after waking from an overnight sleep.

Embodiment 18

The method of embodiment 17, wherein the first dosage form and the second dosage forms are identical, and the second dosage form is administered to the human being about 2 hours to about 6 hours after the first dosage form is administered.

Embodiment 19

The method of embodiment 18, wherein the second dosage form containing reboxetine is administered to the human being about 6 hours after the first dosage form is administered.

Embodiment 20

The method of embodiment 17, wherein the first dosage form and the second dosage forms are not identical, wherein the first dosage form and the second dosage form is administered at about the same time to the human being, and the second dosage form releases reboxetine about 2 hours to about 6 hours after the first dosage form releases reboxetine.

Embodiment 21

The method of embodiment 20, wherein the first dosage form provides immediate release of reboxetine.

Embodiment 22

The method of embodiment 20 or 21, wherein the second dosage form provides delayed release of reboxetine.

Embodiment 23

The method of embodiment 2, 3, 4, 5, 6, 7, 8, 9, 10, 11, 12, 13, 14, 15, or 16, wherein the single dosage form of reboxetine is administered once per day.

Embodiment 24

The method of embodiment 17, 18, 19, 20, 21 or 22, wherein the first dosage form and the second dosage form are each administered once per day.

While the present invention has been shown and described in connection with the embodiments, it will be apparent to those skilled in the art that modifications and variations can be made without departing from the spirit and scope of the invention as defined by the appended embodiments.

The terms "a", "an", "the" and similar referents used in the context of describing the invention (especially in the context of the following embodiments) are to be construed to cover both the singular and the plural, unless otherwise indicated herein or clearly contradicted by context. All method described herein can be performed in any suitable order unless otherwise indicated herein or contradicted by context. The use of any and all examples or exemplary language (e.g., "such as") provided herein is intended merely to better illuminate the invention and does not pose a limitation on the scope of any embodiment. No language in the specification should be construed as indicating any non-embodied element essential to the practice of the invention.

Groupings of alternative elements or embodiments disclosed herein are not to be construed as limitations. Each group member may be referred to and embodied individually or in any combination with other members of the group or other elements found herein. It is anticipated that one or more members of a group may be included in, or deleted from, a group for reasons of convenience.

Certain embodiments are described herein, including the best mode known to the inventors for carrying out the invention. Of course, variations on these described embodiments, will become apparent to those or ordinary skill in the art upon reading the foregoing description. The inventor expects skilled artisans to employ such variations as appropriate, and the inventors intend for the invention to be practiced otherwise than specifically described herein. Accordingly, the embodiments include all modifications and equivalents, or the subject matter recited in the embodiments as permitted by applicable law. Moreover, any combination of the above described elements in all possible variations thereof is contemplated unless otherwise indicated herein or otherwise clearly contradicted by context.

In closing, it is to be understood that the embodiments disclosed herein are illustrative of the principles of the embodiments. Thus, by way of example, but not limitation, alternative embodiments may be utilized in accordance with the teachings herein. Accordingly, the embodiments are not limited to embodiments precisely as shown or described.

The invention claimed is:

1. A pharmaceutical product comprising a single dosage form and a label, wherein the single dosage form comprises a first release component and a second release component, wherein the first release component contains 1 mg to 10 mg of reboxetine, and the second release component contains 0.1 mg to 10 mg of reboxetine and is coated with a polymer that delays release of reboxetine in the second release component;
   wherein the single dosage form has a property that, when administered to a fasted human subject:
   1) the reboxetine in the first release component provides a first local maximum in reboxetine plasma concentration, and
   2) the reboxetine in the second release component provides a second local maximum in reboxetine plasma concentration,
   wherein the first local maximum in reboxetine plasma concentration occurs about 2 hours to about 6 hours prior to the second local maximum in reboxetine plasma concentration;
   wherein reboxetine is the only active pharmaceutical agent; and
   wherein the label states that the single dosage form is to be administered once a day.

2. The pharmaceutical product of claim 1, wherein the polymer that delays release of reboxetine in the second release component comprises an acrylic acid or an acrylate polymer.

3. The pharmaceutical product of claim 1, wherein the polymer that delays release of reboxetine in the second release component comprises a quaternary ammonium compound.

4. The pharmaceutical product of claim 1, wherein the polymer that delays release of reboxetine in the second release component comprises a cellulose derivative.

5. The pharmaceutical product of claim 1, wherein the first release component is free of any polymer that controls or delays release of reboxetine.

6. The pharmaceutical product of claim 1, wherein the single dosage form includes an inner core and an outer coating layer, the inner core includes the second release component containing the reboxetine, and the outer coating layer includes the first release component containing the reboxetine.

7. The pharmaceutical product of claim 6, wherein the polymer that delays release of reboxetine in the second release component is disposed between the inner core containing the reboxetine and the first release component.

8. The pharmaceutical product of claim 1, wherein the single dosage form includes a first controlled release layer including the first release component, and a second controlled release layer including the second release component, and wherein the first controlled release layer and the second controlled release layer together form a bi-layer structure.

9. The pharmaceutical product of claim 8, wherein the first controlled release layer provides immediate release of reboxetine.

10. The pharmaceutical product of claim 1, wherein the single dosage form includes a first release layer including the first release component, and a second release layer including the second release component, and wherein the first release layer is not physically bound to the second release layer.

11. The pharmaceutical product of claim 10, wherein the first release layer provides immediate release of reboxetine.

12. The pharmaceutical product of claim 1, wherein the reboxetine is in the free base form.

13. The pharmaceutical product of claim 1, wherein the reboxetine is in a salt form.

14. The pharmaceutical product of claim 1, wherein the reboxetine is in the form of mesylate salt.

15. The pharmaceutical product of claim 1, wherein the single dosage form is in the form of a pill, a tablet, a capsule, a caplet, or a cachou.

16. The pharmaceutical product of claim 1, wherein the single dosage form further comprises a binder.

17. The pharmaceutical product of claim 1, wherein the single dosage form further comprises a lubricant.

18. The pharmaceutical product of claim 1, wherein the single dosage form further comprises an inert excipient.

19. The pharmaceutical product of claim 1, wherein the first release component contains 3 mg to 7 mg of reboxetine.

20. The pharmaceutical product of claim 1, wherein the second release component contains 0.1 mg to 7 mg of reboxetine.

* * * * *